(12) United States Patent
Sigler et al.

(10) Patent No.: US 7,271,252 B2
(45) Date of Patent: Sep. 18, 2007

(54) REAGENTS FOR DETECTING EFAVIRENZ

(75) Inventors: Gerald F. Sigler, Carmel, IN (US); Mitali Ghoshal, Noblesville, IN (US); Lili Arabshahi, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/420,196

(22) Filed: Apr. 22, 2003

(65) Prior Publication Data

US 2004/0214251 A1  Oct. 28, 2004

(51) Int. Cl.
*C12P 21/08* (2006.01)
*G01N 33/53* (2006.01)

(52) U.S. Cl. .................... 530/388.9; 436/543

(58) Field of Classification Search ........... 530/388.85, 530/391.3, 388.9, 389.8, 807; 436/543, 544, 436/545, 546; 435/345, 961; 424/157, 175.1
See application file for complete search history.

(56) References Cited

U.S. PATENT DOCUMENTS 5,519,021 A * 5/1996 Young et al. ............. 514/230.5
2003/0100088 A1* 5/2003 Sigler et al. ................ 435/184

FOREIGN PATENT DOCUMENTS

| WO | WO 90/15798 | | 12/1990 |
| WO | WO 96/37457 | | 11/1996 |
| WO | WO 99/64048 | * | 12/1999 |
| WO | WO 03/006506 A2 | | 1/2003 |

OTHER PUBLICATIONS

Maurin et al. Kinetics and Mechanism of Hydrolysis of Efavirenz. Pharmaceutical Research, vol. 19, No. 4, Apr. 2002, pp. 517-521.*

Chemical Antibodies, AAL Reference Laboratories, Inc. Nov. 13, 1997, 5 pages.*

Exercise 3, Antigen-Antibody I; LSMUC and the Department of Microbiology, Immunology and Parasitology, 1995, 5 pages.*

Harlow et al. Antibodies: A Laboratory Manual. 1998, pp. 72 and 131.*

Azoulay et al. Immunosassay, a simple and efficient method for plasmatic and intracellular quantification of antiviral drugs. Sixth International Congress of Drug Therapy in HIV infection, Abstract No. P193. Nov. 17-21, 2002.*

Marzolini, Catia et al., "Efavirenz plasma levels can predict treatment failure and central nervous system side effects in HIV-1-infected patients," AIDS 2001, vol. 15, No. 1, pp. 71-75.

Mutlib, A.E. et al., "Identification and characterization of efavirenz metabolites by liquid chromatography/mass spectrometry and high field NMR: species differences in the metabolism of efavirenz," Drug Metabolism and Disposition, vol. 27, No. 11, 1319-1333, 1999.

Rezk, Naser L. et al., "Simple and rapid quantification of the non-nucleoside reverse transcriptase inhibitors nevirapine, delavirdine, and efavirenz in human blood plasma using high-performance liquid chromatography with ultraviolet absorbance detection," Journal of Chromatography B, 774 (200) 79-88.

* cited by examiner

*Primary Examiner*—Bruce Campell
*Assistant Examiner*—Emily M. Le
(74) *Attorney, Agent, or Firm*—Marilyn L. Amick; Roche Diagnostics Operations, Inc.

(57) ABSTRACT

The invention provides derivatives of efavirenz and methods of making derivatives of efavirenz. The derivatives include immunogenic compounds for producing antibodies to efavirenz and labeled efavirenz tracers. These compounds are useful in immunoassay methods for determining efavirenz.

5 Claims, 3 Drawing Sheets

Efavirenz immunogen

Efavirenz BSA screening conjugate

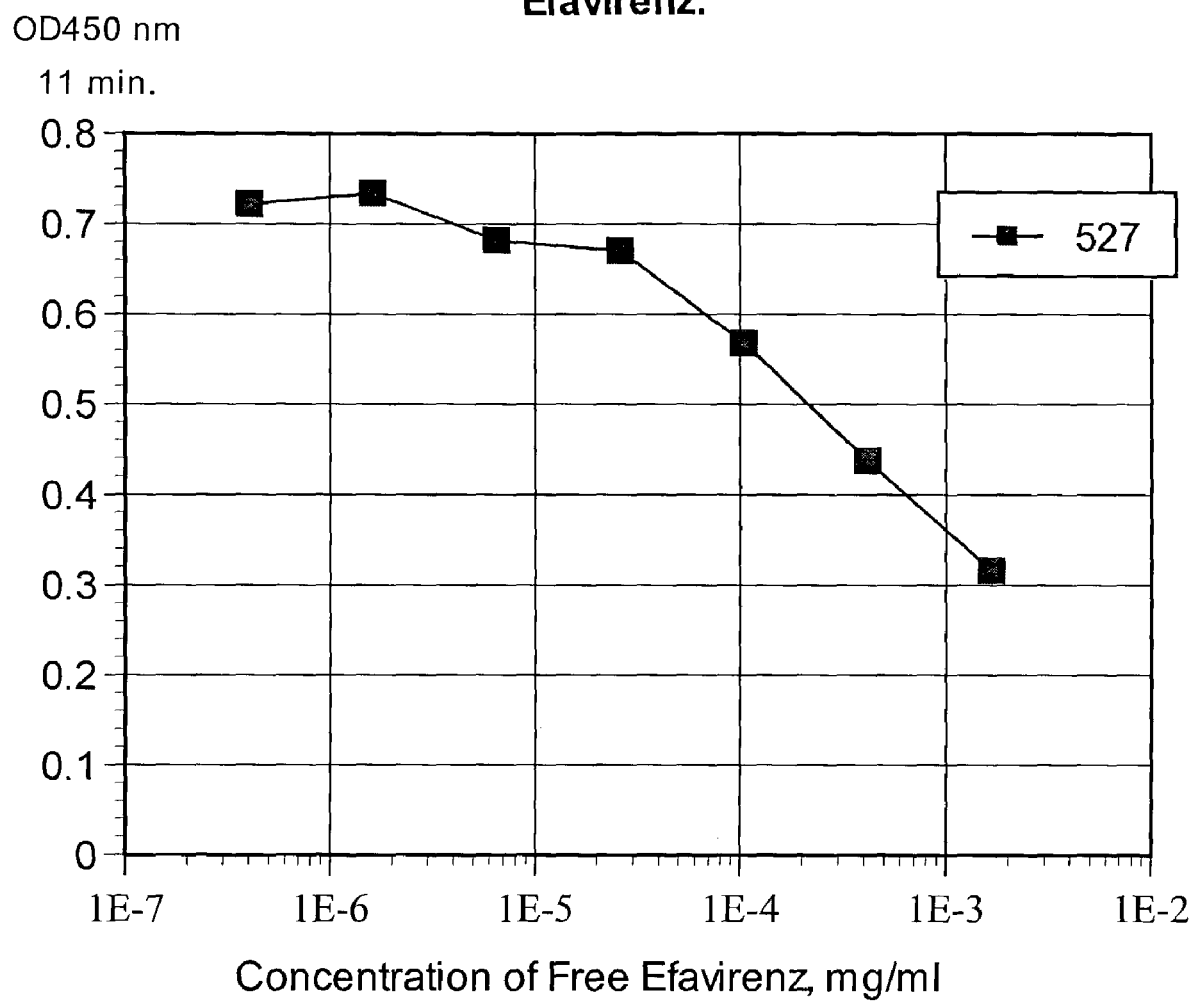

REAGENTS FOR DETECTING EFAVIRENZ

FIELD OF THE INVENTION

The invention relates to immunogens comprising efavirenz and to efavirenz derivatives for use in an immunoassay for the detection of efavirenz.

BACKGROUND OF THE INVENTION

Human immunodeficiency virus type-1 (HIV-1) is a retrovirus that leads to the development of acquired immune deficiency syndrome (AIDS). The infectivity rate of HIV in the United States has been estimated at about 40,000 new infections per year. Current treatments for HIV infection are designed to interfere with the ability of the virus to replicate by inhibiting either HIV protease or HIV reverse transcriptase. (RT).

Efavirenz (SUSTIVA®, Bristol-Meyers Squibb) is one of the FDA-approved drugs used in the treatment of patients infected with HIV. Efavirenz has been shown to lower the amount of HIV in the blood (the "viral load"). When taken with other anti-HIV medicines, efavirenz has been shown to reduce patients' viral load and to increase their CD4 cell count.

Clinical research has demonstrated that HIV can develop resistance to drugs used in HIV therapy, including efavirenz. Such drug resistance is thought to be a primary reason for therapy failure. The development of drug resistance in HIV may be a result of the virus' rapid replication rate. Despite its potency, efavirenz has a low genetic barrier. A high level of phenotypic resistance can be induced by a single mutation, frequently at lysine-103 (K103N) in the RT gene. The emergence of efavirenz-resistant HIV mutants could be a result of repeated exposure to ineffective or sub-therapeutic drug levels.

Therapeutic failures are observed more frequently in patients having low serum concentrations of efavirenz. For example, Marzolini et al., *AIDS* 15 (London), 71-75, 2001, reported virological failure in 50% of patients (85 total patients) that had low plasma levels of efavirenz, e.g., <1000 μg/L. In patients with plasma levels of efavirenz that ranged from 1000-4000 μg/L, or more than 4000 μg/L, they observed virological failure in 18-22% of those patients. Moreover, 20-40% of patients receiving efavirenz reported central nervous system (CNS) side effects that include dizziness, hallucinations, nightmares, and insomnia. While these symptoms are usually mild to moderate in severity and are reported to subside progressively over a few weeks after the initiation of efavirenz therapy, it has been reported that about 4% of patients discontinue therapy because of the severity or persistence of these side effects. CNS toxicity was approximately three times more frequent in patients with high efavirenz levels, e.g., >4000 μg/L, compared with the patients having levels in the 1000-4000 μg/L range. This implies that treatment failure and CNS side effects are associated with low and high efavirenz plasma levels, respectively. The variability of efavirenz levels in individuals strongly supports that the dose adjustment should be based on therapeutic drug monitoring (TDM) in order to optimize beneficial therapeutic effects while minimizing CNS side effects.

As pharmacological differences among patients introduce wide heterogeneity in the response to antiviral therapy, monitoring of drug levels could be useful in the management of HIV infection as well as the disorders and diseases associated with HIV infection. Formal therapeutic drug monitoring of antiviral drugs useful in HIV therapy is known using high-performance liquid chromatographic (HPLC) methods (Marzolini et al., ibid.).

While HPLC methods can be used to determine efavirenz levels in plasma, such methods are impractical for commercial use due to, for example, long sample preparation time, long assay time, high cost, and labor-intensive procedures. Thus, a simple and fast analytical method for measurement of plasma levels of efavirenz is needed for effective TDM. Immunoassay techniques are well suited for such analytical applications.

SUMMARY OF THE INVENTION

The invention provides a compound having the structure

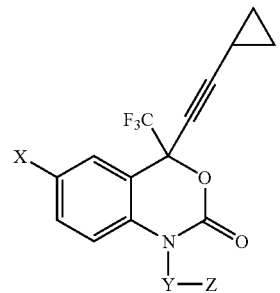

wherein Y is a saturated or unsaturated, substituted or unsubstituted, straight or branched chain of up to 20 carbon atoms and heteroatoms; Z is an active ester, $NH_2$, imidazolide, maleimide, thiol, isothiocyanate, isocyanate, or W, where W is an immunogenic carrier or a label; and X is selected from the group consisting of halogens, $NO_2$, $NH_2$, $CH_3$, and $OCH_3$.

In one aspect of the invention, the carrier is a poly(amino acid). The label may be an enzyme, fluorogenic compound, chemiluminescent material, electrochemical mediator, particle, reporter group, enzyme inhibitor, and nucleic acid.

BRIEF DESCRIPTION OF THE FIGURES

FIG. 3 shows the competitive inhibition of binding of serum antibody to N-linked BSA-efavirenz by free efavirenz.

DETAILED DESCRIPTION OF THE INVENTION

Figure 1:
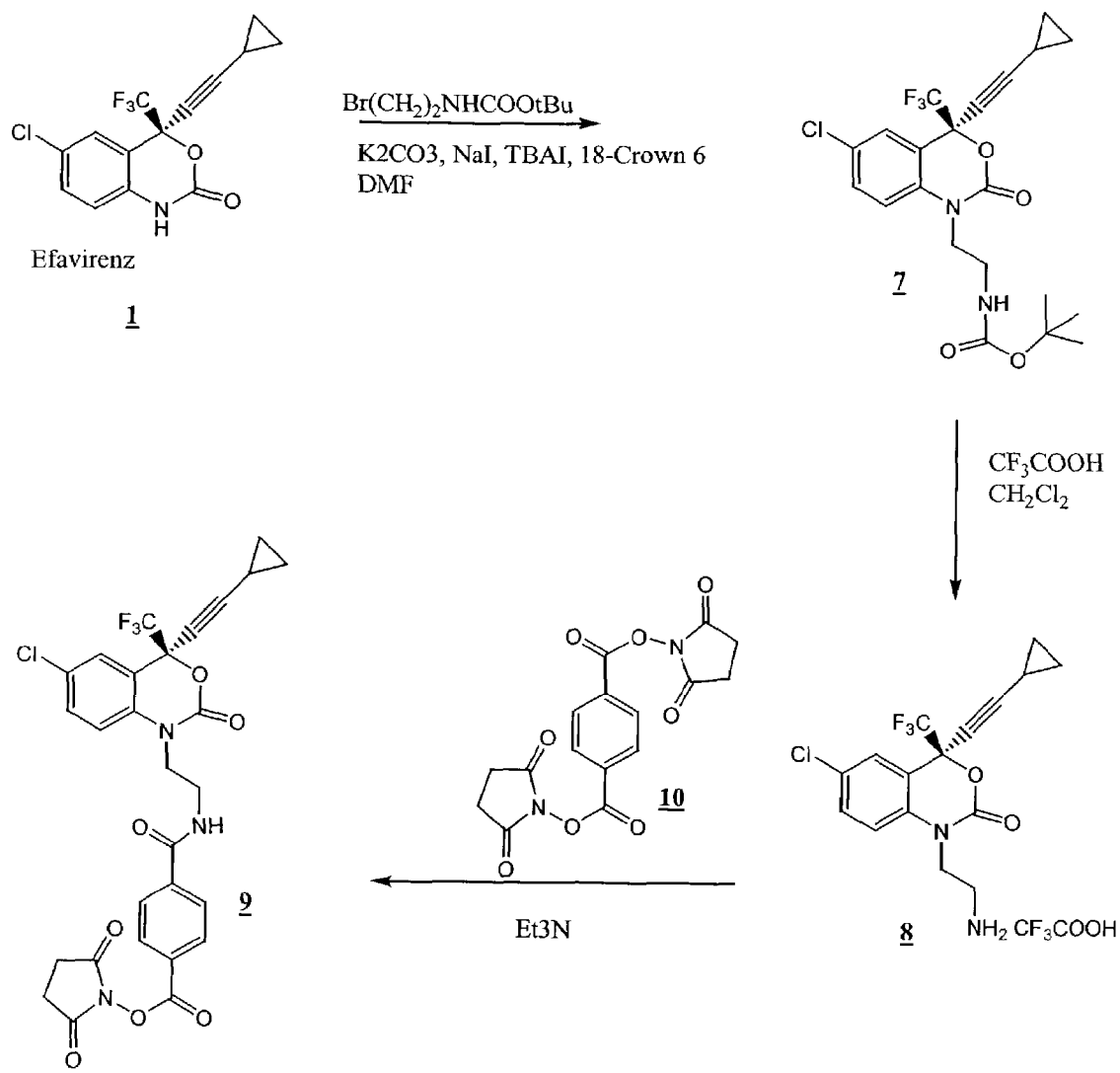
FIG. 1 is a schematic representation of a synthesis method for an N-hydroxysuccinimide ester derivative according to the invention.

Before proceeding with the description of the specific embodiments, a number of terms will be defined.

"Efavirenz" refers to the compound that is the active ingredient in SUSTIVA® (Bristol-Meyers Squibb), an FDA-approved drug used in the treatment of patients infected with HIV, the virus that can lead to development of AIDS. Efavirenz can be represented by the chemical structure:

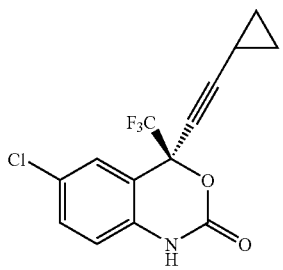

The term "efavirenz" can be taken to encompass compounds that have the same substantial structure, including both chiral and racemic mixtures of the above structure, metabolites, and analogues thereof. For instance, it is understood that the chlorine may be replaced with another halogen, a nitro group, an amino group, a methyl group, or a methoxy group, provided a molecule with some efficacy is obtained. Other groups that may replace the chlorine atom, or other atoms that may be substituted on the efavirenz molecule, may be known or may become known in the art of pharmaceutical chemistry. The invention is intended to encompass all known or future discovered molecules substantially similar to efavirenz.

"Haptens" are partial or incomplete antigens. They are protein-free substances, mostly low molecular weight substances, which are not capable of stimulating antibody formation, but which do react with antibodies. The latter are formed by coupling a hapten to a high molecular weight carrier and then injecting this coupled product, i.e., immunogen, into a human or animal subject. Efavirenz is a hapten.

The term "derivative" refers to a chemical compound or molecule made from a parent compound or molecule by one or more chemical reactions.

An "activated hapten" refers to a hapten derivative that has been provided with an available site for reaction, such as by the attachment of a linking group, for synthesizing a hapten derivative conjugate.

As used herein, a "linking group" or "linker" refers to a portion of a chemical structure which connects two or more substructures such as haptens, carriers, immunogens, labels, tracers or other linkers. A linking group has at least 1 uninterrupted chain of atoms other than hydrogen (or other monovalent atoms) extending between the substructures. The atoms of a linking group and the atoms of a chain within a linking group are themselves connected by chemical bonds. Linkers may be straight or branched, saturated or unsaturated, carbon chains. They may also include one or more heteroatoms within the chain or at termini of the chains. By "heteroatoms" is meant atoms other than carbon which are chosen from the group consisting of oxygen, nitrogen and sulfur. Linking groups may also include cyclic or aromatic groups as part of the chain or as a substitution on one of the atoms in the chain.

The number of atoms in a linking group or linker is determined by counting the atoms other than hydrogen. The number of atoms in a chain within a linking group is determined by counting the number of atoms other than hydrogen along the shortest route between the substructures being connected.

Linking groups may be used to activate, e.g., provide an available site on a hapten for synthesizing a conjugate of a hapten with a label or carrier.

The terms "immunogen" and "immunogenic" as used herein refer to substances capable of producing or generating an immune response in an organism.

An "active ester" refers to an ester group that can react with a free amino group of compounds such as, for example, peptides and proteins. Examples of active esters include N-hydroxysuccinimide, p-nitrophenyl, pentafluorophenyl, and N-hydroxybenzotriazolyl.

A "carrier" or "immunogenic carrier," as the terms are used herein, is an immunogenic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, and nucleic acids that are recognized as foreign and thereby elicit an immunologic response from the host.

Various protein types may be employed as a poly(amino acid) immunogenic carrier. These types include albumins, serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic poly(amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums such as gum arabic, agar, and so forth. The polysaccharide can also contain polyamino acid residues and/or lipid residues.

The immunogenic carrier can also be a poly(nucleic acid) either alone or conjugated to one of the above mentioned poly(amino acids) or polysaccharides.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, a receptor, or a hapten radioactive isotope.

Particles are generally at least about 0.02 microns (μm) and not more than about 100 μm, and usually about 0.05 μm to 10 μm in diameter. The particle can be organic or inorganic, swellable or non-swellable, porous or non-porous, optionally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. Particles can also be comprised of organic and inorganic polymers, liposomes, latex, phospholipid vesicles, or lipoproteins.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, urine, tears, cells, organs, tissues, bone, bone marrow, lymph, lymph nodes, synovial tissue, chondrocytes, synovial macrophages, endothelial cells, and skin.

The term "patient" includes human and animal subjects.

The present invention provides efavirenz hapten derivatives that are useful for the preparation of immunogens and conjugates for use in immunoassays for the detection of efavirenz.

By attaching an efavirenz derivative according to the present invention to an immunogenic carrier material, antisera and polyclonal antibodies, as well as monoclonal antibodies, can be produced and isolated, which are useful reagents for immunoassays for the detection of efavirenz.

The derivatives can also be coupled to a variety of labels by methods well known in the art to provide a variety of reagents useful in various immunoassay formats. For detection, there can be attached detector molecules such as fluorophores, for example fluorescein, or radiolabelled or chemiluminescent groups to produce tracers. The hapten can be bound to microparticles including colored latex for use in spectrophotometric or direct optical detection formats such as latex agglutination and chromatographic strip tests. The attached group may also be an indirect detection molecule such as an energy transfer partner, enzyme or other group which is detected by further chemical reaction.

Coupling can be accomplished by any chemical reaction that will bind the label or carrier. This linkage can include many chemical mechanisms, for instance covalent binding, affinity binding, intercalation, coordinate binding, and complexation. Most often, the linkage is made through covalent bonding. Covalent binding can be achieved either by direct condensation of existing side chains or by incorporation of external bridging molecules. Many bivalent or polyvalent linking agents are useful in coupling protein molecules, such as a carrier, to other molecules. Representative coupling agents include organic compounds such as thioesters, carbodiimides, N-hydroxysuccinimide esters, diisocyanates, glutaraldehyde, diazobenzenes, and hexamethylene diamines. This listing is not an exhaustive compilation of the various classes of coupling agents known in the art but, rather, is representative of the more common coupling agents. (See Killen and Lindstrom, "Specific killing of lymphocytes that cause experimental autoimmune myasthenia gravis by toxin-acetylcholine receptor conjugates," *J. Immunol.* 133:1335-2549, 1984; Jansen, F. K., Blythman, H. E., Carriere, D., Casella, P., Gros, O., Gros, P., Laurent, J. C., Paolucci, F., Pau, B., Poncelet, P., Richer, G., Vidal, H., and Voisin, G. A., "Immunotoxins: Hybrid molecules combining high specificity and potent cytotoxicity." *Immunological Reviews* 62:185-216, 1982; and Hermanson, G., "Bioconjugate Techniques", Academic Press, 1995.

In one aspect, the invention provides a compound of the formula:

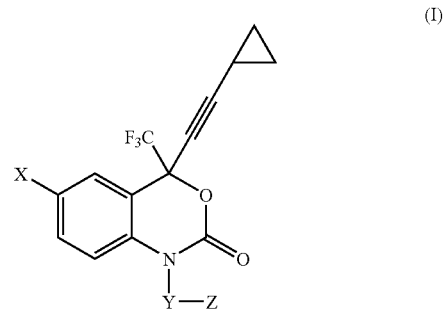

wherein Y is a saturated or unsaturated, substituted or unsubstituted, straight or branched chain of up to 20 carbon atoms and heteroatoms; Z is an active ester, $NH_2$, imidazole, maleimide, thiol, isothiocyanate, isocyanate, or W, where W is an immunogenic carrier or a label; and X is selected from the group consisting of halogens, $NO_2$, $NH_2$, $CH_3$, and $OCH_3$.

In one aspect, the synthesis of efavirenz derivatives involves the direct alkylation of efavirenz. The alkylation may be obtained with a haloalkyl ester or a haloalkyl compound with a proper functional group that may be modified or extended to obtain an activated efavirenz. Synthesis of non-limiting representative compounds of Formula (I) is described in FIGS. 1 and 2.

Novel hapten derivatives, such as alkylated efavirenz, may be prepared under mild conditions using a bifunctional haloalkyl linker which contains a protected functionality at the end opposite the halogen atom. Examples of protected functionalities are protected amines and carboxylic acids. Some examples of bifunctional haloalkyl linkers having a carboxylic acid functionality include alkyl(halo)butyrates wherein the alkyl is methyl, ethyl, propyl or t-butyl, and the halo is chloro, bromo or iodo. Other examples of bifunctional haloalkyl linkers will be readily apparent to those skilled in the art. Some examples of bifunctional haloalkyl linkers having an amine functionality include haloalkyl chains with a t-BOC (acid labile), a phthalimide, or FMOC (base labile) protecting group. One example of a phthalimido alkylating agent is N-iodopropyl-phthalimide (Example 6). FIG. 1 shows alkylation with a t-BOC protected haloalkyl amine.

Alkylation may be accomplished by a reaction in which an alkali metal carbonate is used as base in the presence of a phase transfer catalyst such as a crown ether and sodium iodide. In one aspect, an alkali metal carbonate/crown ether combination is potassium carbonate and 18-crown-6. The reaction is performed in a dipolar aprotic solvent such as dimethylformamide (DMF) at a temperature range of 60-150° C., usually about 120° C., for 1-24 hours. The alkylated product is then isolated, and the protecting group is removed from the linking group under conditions that do not give rise to side-reactions on the efavirenz. Examples of such conditions are saponification with lithium hydroxide to remove an alkyl ester and generate free carboxylic acid and trifluoroacetic acid treatment to remove a t-butyl ester protecting group and generate free amine. Reactions with various protective groups are described in "Protective Groups in Organic Synthesis," T. Green and P. Wuts, eds., Wiley-Interscience, 1991, which is incorporated herein by reference in its entirety.

In another aspect, an N-alkylation product of efavirenz can be obtained by a Michael reaction of efavirenz with an alkyl acrylate in the presence of a base. See, for example, *Chemical and Pharmaceutical Bulletin* 38 (6), 1575-78, 1990, which is incorporated herein by reference in its entirety.

The alkylated efavirenz with a free carboxyl group or an amine terminus may be used directly for preparation of conjugates. For example, efavirenz with carboxyl linking groups may be conjugated to amines on carriers, labels or tracers using condensation reagents well known in the art for formation of amide bonds. Similarly, amine groups may be conjugated to carboxyl groups on carriers, labels, or tracers. In addition, in one aspect of the invention, the alkylated efavirenz with free carboxyl or amine terminus is attached to a second linking group to generate terminal activating groups such as, for example, active esters, isocyanates, imidazolide, isothiocyanates, thiols and maleimides. These second linking groups may also be a variety of heterobifunctional or homobifunctional linkers which are well-known in the art. For instance, in the case of a first linking group which terminates in a carboxyl group, examples of second linking groups include maleimidoalkylamines as described in PCT publication WO 90/15798 and amino acids. These amine-containing second linking groups are typically reacted with a carboxyl group on the first linker using any one of a large number of condensation reagents known in the art for formation of amide bonds. In the case where the first linker terminates in an amine, examples of second linkers include terephthalic acid di-N-hydroxysuccinimide ester, 1,1'-biphenyl-4,4'-di-N-hydroxysuccinimide, 4-isothiocyanato-benzoylchloride, 3-maleimidopropionic acid N-hydroxysuccinimide ester (MPS), and S-acetylthiopropionic acid-N-hydroxysuccinimide ester (SATP). The N-hydroxysuccinimide ester second linkers are typically reacted directly with the amine-containing first linker under mild conditions, such as, for example, in a dipolar aprotic solvent at room temperature or below in the presence of triethylamine. For example, FIG. 1 shows the reaction of the second linker with the amino terminus of the first linker in the presence of triethyl amine.

In the case of a di-N-hydroxysuccinimide ester, the reaction is carried out under conditions which favor the formation of a mono-substituted product rather than a di-substituted product. For example, dropwise addition of the efavirenz linker amine to di-N-hydroxysuccinimide ester will favor mono-substitution. After attachment of the second linker to the efavirenz, a new terminal functional group on the second linker is present. In the case of di-N-hydroxysuccinimide ester second linkers, the new terminal functional group is simply the unreacted N-hydroxysuccinimide ester obtained from mono-substitution. This latter group is ready for conjugation to amine groups on carriers, labels and tracers by direct condensation to give amide bonds. Similarly, when the terminal linker group is an isothiocyanate, direct conjugation to amine groups on carriers, labels and tracers may be performed to give thiourea bonds.

In the case where the new terminal functional group is a maleimide, as with MPS, conjugation is accomplished by addition to thiol groups on carriers, labels and tracers to give thioether bonds. The thiol groups may be inherent to the carriers, labels and tracers or may be introduced by thiolating agents such as 2-iminothiolane (2-IT), succinimidyl acetylthiopropionate (SATP) and succinimido 2-pyridyldithiopropionate (SPDP). The incipient thiol group is then available to form thiol ethers with maleimide. In another aspect, bromoacetylated modified carriers or labels will form a thiol ether.

In the case where the new functional group is a thiol or protected thiol as with SATP, the thiol is conjugated directly or subsequent to deprotection with a maleimide-modified immunogen or label. Many more variations of linker chemistries will be obvious to those skilled in the art, and these are only presented for the sake of illustration. A comprehensive treatment of homobifunctional and heterobifunctional linking groups and the reaction conditions for their attachment to amines and carboxylic acids is provided in "Bioconjugate Techniques", G. Hermanson, Academic Press, 1995, which is incorporated herein by reference in its entirety.

In another aspect, acylated derivatives with urea or thiourea bonds at the point of attachment to the amino-linked efavirenz are generated by reacting the amino functionality of an efavirenz derivative with 4-nitrophenylchloroformate, phosgene, or thiophosgene. The later intermediates react readily with amines (from aminodextrans, proteins, or peptides) to give ureas or thioureas. Alternative phosgene equivalents such as carbonyldiimidazole or disuccinimidyl carbonate will react similarly.

Figure 2:
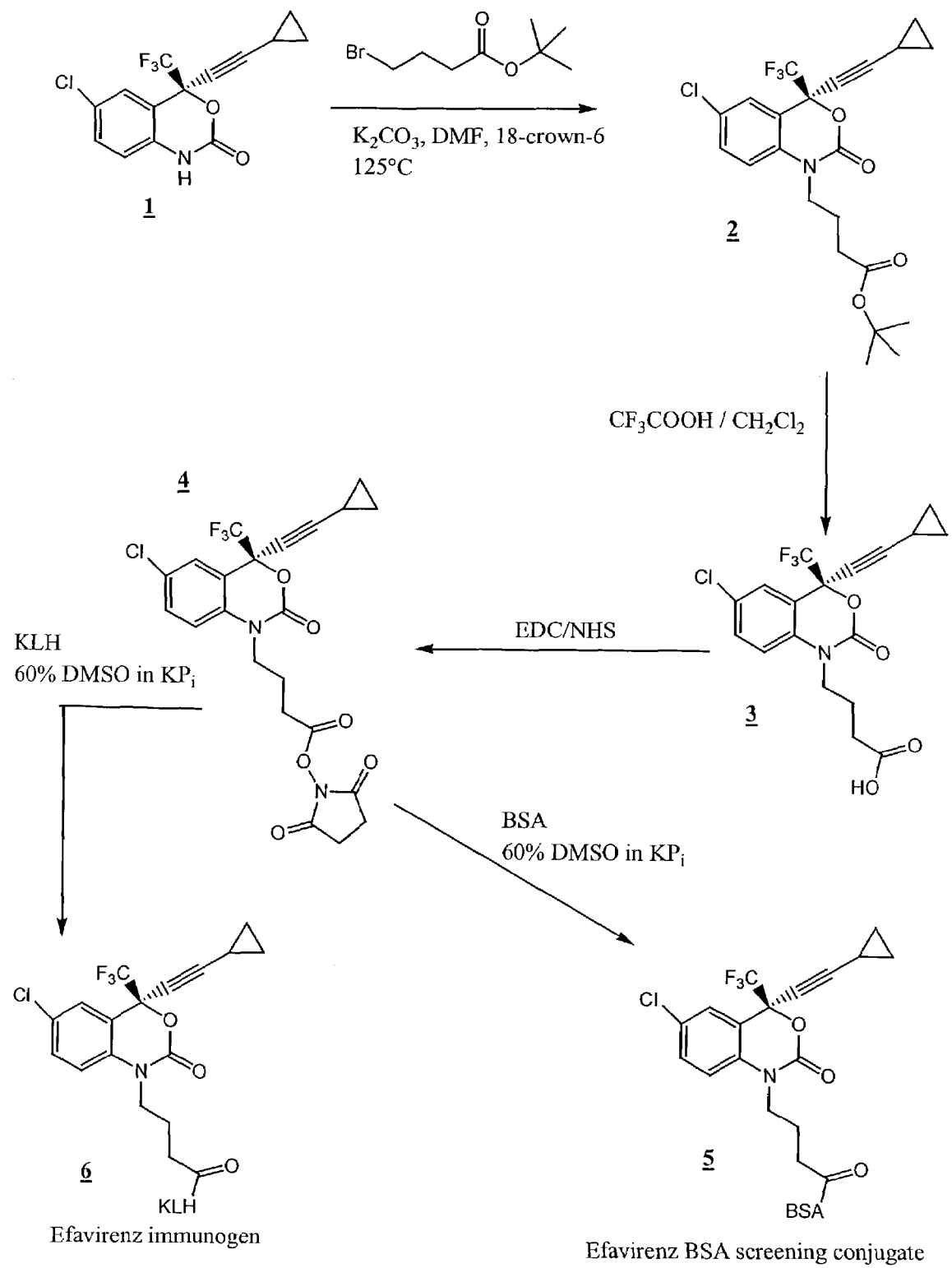
FIG. 2 is a schematic representation of a synthesis method for an immunogen and a conjugate according to the invention.

Efavirenz derivatives comprising a linker with an active esters are reactive with nucleophiles, especially primary amines, at relatively low temperature in a variety of aqueous and non-aqueous solvent mixtures. As shown in FIGS. 1 and 2, the reaction between an efavirenz activated ester derivative and amino groups on a carrier is typically carried out in a buffered mixture of water and a water miscible organic solvent such as DMSO in potassium phosphate buffer ($KP_i$) at room temperature for 0.5-5 days. The pH of the buffer is typically between 6 and 8 for active esters, isocyanates, and isothiocyanates.

In preparing the immunogens of the invention, a carrier poly(amino acid) or other substance having immunogenic properties is coupled to an activated efavirenz derivative. In one aspect, a protein carrier may be employed, including, for example, albumins, serum proteins, e.g., globulins, ocular lens proteins, lipoproteins, and the like. Illustrative protein carriers include keyhole limpet hemocyanin (KLH), bovine serum albumin (BSA), egg ovalbumin, bovine gamma-globulin (BGG), etc. Alternatively, synthetic poly(amino acids) may be employed, as may other synthetic or natural polymeric materials bearing reactive functional groups. In order to generate antibodies, the immunogen is injected into a host animal. The immunogen may be administered at a variety of sites, in several doses, one or more times, over many weeks.

The hapten derivatives can also be coupled to a variety of tracer, detection or labeling molecules by methods well known in the art to provide a variety of reagents useful in different immunoassay formats. For detection, there can be attached detector molecules such as fluorophores, for example fluorescein, or radiolabeled or chemiluminescent groups to produce tracers. The hapten can be bound to microparticles including colored latex for use in spectrophotometric or direct optical detection formats such as latex agglutination and chromatographic strip tests. The attached group may also be an indirect detection molecule such as an energy transfer partner, enzyme, or other group that is detected by further chemical reaction.

The following examples serve merely to illustrate certain aspects of the invention and should not be viewed as limiting the invention in scope or spirit.

EXAMPLE 1

Synthesis of 4-(6-chloro-4-cyclopropylethynyl-2-oxo-4-trifluoromethyl-4H-benzo[d][1,3]oxazin-1-yl)-butyric acid tert-butyl ester (2)

To 250 mg (0.79 mmol) of efavirenz 1 was added 10 mL of anhydrous DMF, 600 mg (4.34 mmol) of potassium carbonate, 120 mg (0.80 mmol) of sodium iodide and 492 mg (2.2 mmol) of 4-bromo-butyric acid tert-butyl ester followed by 5 mg of 18-crown-6. The mixture was heated to 125° C. for 2 hours under argon atmosphere and concentrated under reduced pressure. To the residue 50 mL of chloroform was added, and the solid was filtered off. To the filtrate 50 mL of water was added. The organic layer was separated, washed with 50 mL of water, dried ($Na_2SO_4$), and concentrated. The residue was purified by silica gel flash column chromatography in 70% ethyl acetate in hexane to give 327 mg (0.721 mmol, 90% yield) of 2 (M+Na, 480).

EXAMPLE 2

Synthesis of 4-(6-chloro-4-cyclopropylethynyl-2-oxo-4-trifluoromethyl-4H-benzo[d][1,3]oxazin-1-yl)-butyric acid (3)

To 290 mg (0.63 mmol) of 2 was added 6 mL of dichloromethane and 6 mL of trifluoroacetic acid. The reaction mixture was allowed to stir at room temperature for 30 minutes and concentrated under reduced pressure. To the residue was added 40 mL of dichloromethane, which was subsequently concentrated under reduced pressure. The above process of addition of dichloromethane and concentrating under reduced pressure was repeated four more times to give 240 mg (0.59 mmol, 94% yield) of 3 as a thick gum (M+H, 402).

EXAMPLE 3

Synthesis of 4-(6-chloro-4-cyclopropylethynyl-2-oxo-4-trifluoromethyl-4H-benzo[d][1.3]oxazin-1-yl)-butyric acid N-hydroxysuccinimide ester (4)

To a solution of 200 mg (0.49 mmol) of 3 in 30 mL of dichloromethane (distilled over $CaH_2$) was added 225 mg (1.2 mmol) of 1-ethyl-3-(3-dimethylaminopropyl)-carbodiimide (EDC) and 102 mg (0.88 mmol) of N-hydroxysuccinimide (NHS). The reaction mixture was allowed to stir at room temperature 18 hours under an argon atmosphere. To this reaction mixture was added 40 mL of dichloromethane, and the organic layer was washed with 2×50 mL of water and 2×50 mL of saturated sodium bicarbonate followed by 75 mL of water. The organic layer was dried ($Na_2SO_4$) and concentrated to give the crude activated ester. This was purified by silica gel chromatography using 50% ethyl acetate in hexane to give 98 mg (0.19 mmol, 39% yield) of 4 as white powder (M+H, 499).

EXAMPLE 4

Synthesis of [2-(6-chloro-4-cyclopropylethynyl-2-oxo-4-trifluoromethyl-4H-benzo[d][1,3]oxazin-1-yl)-ethyl]-carbamic acid tert-butylester 7

To a solution of 250 mg of efavirenz in 10 mL of anhydrous DMF was added 600 mg of anhydrous $K_2CO_3$, 120 mg NaI, 490 mg of 2-(BOC-amino)ethyl bromide and 5 mg of 18-crown-6. The reaction mixture was heated at 125° C. for 2 hours. The reaction mixture was cooled to room temperature, and 1 g of 2-(BOC-amino)ethyl bromide and 20 mg of tetrabutylammonium iodide were added and allowed to stir at room temperature 18 hours. The reaction mixture was analyzed by reverse-phase high performance liquid chromatography (RP-HPLC, C-18 Vydac 218TP54 (4.6 mm×250 mm) using a gradient run with water-acetonitrile mixtures containing 0.1% trifluoroacetic acid (0-100% AcCN-0.1% TFA in 20 minutes). This indicated the formation of product with a substantial amount of efavirenz in the reaction mixture. An additional 1 g of 2-(BOC-amino) ethyl bromide was added, and the reaction mixture was heated at 60° C. for 18 hours. The reaction mixture was cooled to room temperature and filtered. The filtrate was concentrated, and the residue was purified by preparative RP-HPLC using a gradient run ($CH_3CN$/water containing 0.1% trifluoroacetic acid). The column used was a Rainin C-18 (ODS) 60 Å (21.4×250 mm). The desired fractions were combined, concentrated in the rotary evaporator, and then lyophilized to give 25 mg of the desired product 7 as a white solid (M+Na, 481).

EXAMPLE 5

Synthesis of 1-(2-amino-ethyl)-6-chloro-4-cyclopropylethynyl-4-trifluoromethyl-1,4-dihydro-benzo[d][1,3]oxazin-2-one trifluoroacetate 8

To 2.5 mg of 7 was added 500 µL of dichloromethane and 500 µL of trifluoroacetic acid. The mixture was allowed to stir at room temperature for 30 minutes and concentrated under reduced pressure to give 3 mg of 8 as a thick oil (M+H, 359).

EXAMPLE 6

Synthesis of 2-[3-(6-chloro-4-cyclopropylethynyl-2-oxo-4-trifluoromethyl-4H-benzo[d][1,3]oxazin-1-yl)-propyl]-isoindole-1,3-dione To a solution of 50 mg (0.15 mmol) of efavirenz in 2 mL of anhydrous DMF was added 120 mg of potassium carbonate and 1 mg of 18-crown-6 followed by 50 mg (0.15 mmol) of 3-iodopropyl phthalimide. The resulting reaction mixture was heated at 60° C. for 18 hours and concentrated under reduced pressure. To the residue 10 mL of dichloromethane was added and filtered. The filtrate was concentrated, and to the residue 75 mL of $CHCl_3$ and 50 mL of water were added. The organic layer was separated, and the aqueous layer was extracted 2×40 mL of $CHCl_3$. The combined organic layers were dried and concentrated to give 40 mg of desired product as a thick gum. This was purified by preparative RP-HPLC using a gradient run ($CH_3CN$/water containing 0.1% trifluoroacetic acid). The column used was a Rainin C-18 (ODS) 60° A (21.4×250 mm). The desired fractions were combined, concentrated in the rotary evaporator, and then lyophilized to give 10 mg of the desired product (M+H, 503).

EXAMPLE 7

N-[2-(6-chloro-4-cyclopropylethynyl-2-oxo-4-trifluoromethyl-4H-benzo[d][1,3]oxazin-1-yl)-ethyl]-terephthalamic acid N-hydroxysuccinimide ester 9

To 15 g (73.8 mmol) of terephthaloyl chloride was added 300 mL of methylene chloride, and the solution was cooled to 0° C. for about 10 minutes. To this solution was added 30 g of N-hydroxysuccinimide followed by 30 mL of triethylamine dropwise. The mixture was allowed to stir at 0° C. for 1 hour and at room temperature for 48 hours. The reaction mixture was filtered, and the residue was washed with 200 mL of methylene chloride. The solid was resuspended in 300 mL of methylene chloride and allowed to stir for 10 minutes at room temperature. The solid was filtered and dried under vacuum to give 24.1 g (67 mmol, 90%) of terephthalic acid di-N-hydroxysuccinimide ester (10).

To 1.0 mmol of terephthalic acid 1,4-di-N-hydroxysuccinimide ester (10) is added 100 mL of dry THF. In another flask is added 1.0 mM of efavirenz amine 8 in 60 mL of dry THF and 2.0 mL of triethylamine. This efavirenz amine solution is added to the di-NHS ester solution dropwise over a period of 30 minutes under argon atmosphere. The reaction is stirred at room temperature overnight. The reaction is concentrated under reduced pressure. The residue is purified by silica gel flash column chromatography using a mixture of THF and ethyl acetate to yield the desired product 9.

EXAMPLE 8

Efavirenz-BSA Conjugate (5)

A solution of 500 mg of bovine serum albumin (BSA) in 7 mL of 50 mM potassium phosphate (pH 7.5) was cooled in an ice bath. To the solution was added, dropwise, 7 mL of DMSO, maintaining the reaction mixture temperature below room temperature. To the protein solution was added a solution of 9.4 mg (0.019 mmol) of 4 in 1.5 mL of anhydrous DMF (dropwise). The reaction mixture was allowed to stir at room temperature for 48 hours. The resulting conjugate was placed in a dialysis tubing (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature followed by 6 changes with 50 mM potassium phosphate (pH 7.5) at 4° C. (1 L each). The protein concentration was determined to be 23.2 mg/mL using Biorad Coomassie blue protein assay (Bradford, M., *Anal. Biochem.* 72, 248, 1976). A total of 20 mL of the conjugate was obtained.

EXAMPLE 9

Efavirenz-KLH Conjugate (6)

A solution of 151 mg of keyhole limpet hemocyanine in 7 ml of 50 mM potassium phosphate (pH 7.5) was cooled in an ice bath. To the solution was added 8.5 mL of DMSO dropwise, and the reaction temperature was maintained below room temperature. To the protein solution was added a solution of 44 mg (0.088 mmol) of 4 in 1.5 mL of DMF dropwise. The mixture was allowed to stir at room temperature 18 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (1 L each). The protein concentration was determined to be 4.2 mg/mL using Biorad Coomassie blue protein assay. A total of 28 mL of the conjugate was obtained. The extent of available lysine modification was determined to be 74% by the TNBS method (Habeeb AFSA, *Anal. Biochem.* 14, 328-34, 1988).

EXAMPLE 10

Development of Antisera to Efavirenz

Immunizations

Female Balb/c mice, of at least 20 weeks age, were initially immunized with the efavirenz N-linked KLH conjugate 6 by the following method. The conjugate 6 was diluted to 0.2 mg/mL in physiological saline solution. 0.3 mL of the diluted conjugate was drawn up into a 0.5 mL syringe. 0.3 mL of Complete Freund's Adjuvant (Sigma Chemicals) was drawn up into a separate 0.5 mL syringe. The two syringes were connected by means of a double hubbed 25 ga stainless steel needle. The emulsion was prepared by repeatedly forcing the contents from one syringe to the other until a definite stiffness in the mixture could be felt. The entire contents were then forced into one syringe. A 27 ga needle was attached to the syringe containing the emulsion. The mice were injected with a total of 100 µL of the resulting emulsion, divided into subcutaneous and intraperitoneal sites.

The above procedure was repeated after 30 and 60 days, with the substitution of Incomplete Freund's Adjuvant (Sigma) for Complete Freund's Adjuvant.

Testing for Competitive Inhibition

Fourteen days subsequent to the last immunization, serum samples were taken from the mice via retro-orbital bleeds. Approximately 15-20 µL of clarified serum was obtained after separation of cellular materials by centrifugation. The serum was immediately diluted 1:10 into phosphate buffered saline (PBS), pH 7.4, containing 0.02% thimerosal (PBS-T) to prevent microbe growth.

The sera were titered for antibody activity via an antigen specific ELISA. Wells of a styrene 96-well plate were coated with efavirenz N-linked BSA conjugate 5 by placing 50 µL of a 0.1 µg/mL efavirenz-BSA conjugate solution into 0.1 M potassium carbonate, pH 9.2, in the wells and incubating the covered plate at 37° C. for 1 hour. The solution was removed, and the wells were immediately filled with a post coat solution consisting of 1% gelatin hydrolysate, 2% sucrose, 0.1 M Tris buffer, pH 7.4, and 0.15% TWEEN 20 (all reagents from Sigma Chemical Co.), covered and incubated as above. Subsequently, the plates were rinsed once with 2% sucrose and air-dried. Once dry, the plates were sealed into aluminum foil clad plastic bags with a desiccant and stored at 4° C. until used.

Titering consisted of preparing an initial 1:100 dilution of the sera in PBS-T, then seven serial 1:3 dilutions. Fifty microliters of the dilution series of each serum sample was transferred into the wells of a coated microtiter plate, the plate covered and incubated 2 hours at 37° C. The sera dilutions were washed from the wells with PBS-T followed by addition of 50 μL of a 1:5,000 dilution of goat anti-mouse IgG-HRP conjugate (Zymed, Inc.) in PBS-T to each well. The plate was covered and incubated 1 hour at 37° C. After incubation, the plate was washed in PBS-T, and 50 μL of K Blue substrate (Neogen) was added. The color was allowed to develop for 6 minutes at room temperature, after which the reaction was halted by the addition of 50 μL of 1 N HCl. Color that developed was read in a microplate reader equipped with a 450 nm filter. The color intensities were plotted versus the final serum dilutions, and the dilution point at which 50% of the maximum reading was obtained was recorded.

For determining competitive inhibition, plates treated as above were used. Serial 1:4 dilutions of free efavirenz (stock concentrate 1 mg/mL) were prepared after an initial 1:300 dilution into PBS-T. Twenty-five microliters of each dilution of free drug was pipetted into a column of wells on the coated plate. Serum dilutions of twice the concentration determined above were then prepared, and 25 μL was placed into each well of the column. Each column was devoted to a separate mouse serum sample. The plate was covered and allowed to incubate at 37° C. for one hour, after which it was washed with PBS-T. Each well then received 50 μL of a 1:5,000 dilution of the goat anti-mouse IgG-HRP conjugate, covered, and incubated for 1 hour. After incubation, the plate was washed and developed for 11 minutes, then stopped as above. The $OD_{450}$ was plotted as a function of final drug concentration.

The results taken from one mouse are presented in FIG. 3. The addition of free drug confers a competitive inhibition of binding of the serum antibodies to the drug conjugate absorbed to the microplate. The data shows that antibody generated is specific for efavirenz. Of note, the antisera were raised using a chiral drug conjugate, tested versus binding to a chiral BSA conjugate, and the competing drug was chiral. The results indicate that administration of the efavirenz-KLH conjugate was sufficient to produce antibodies specific to the drug portion.

What is claimed is:
1. A compound having the structure

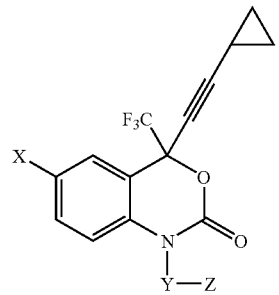

wherein Y is a saturated or unsaturated, substituted or unsubstituted, straight or branched chain of up to 20 carbon atoms:

Z is an active ester, imidazole, maleimide, thiol, isothiocyanate, isocyanate, or W, where W is an immunogenic carrier or a label, wherein the label is selected from the group consisting of enzymes, enzyme fragments, radioactive isotopes, enzyme substrates, enzyme inhibitors, coenzymes, fluorogenic compounds, chemiluminescent materials, reporter groups, nucleic acids and particles, wherein the particles are organic or inorganic and from about 0.02 to about 100 microns in size; and X is selected from the group consisting of halogens, $NO_2$, $NH_2$, $CH_3$, and $OCH_3$.

2. The compound of claim 1 wherein X is Cl.

3. The compound of claim 1 wherein W is an immunogenic carrier selected from the group consisting of poly (amino acids), polysaccharides, and poly(nucleic acids).

4. The compound of claim 1 wherein Z is an active ester selected from the group consisting of N-hdroxysuccinimidyl, p-nitrophenyl, pentafluorophenyl, and N-hvdroxybenzotriazolyl esters.

5. The compound of claim 1, wherein Y is —$(CH_2)_3$—.

* * * * *